Thyagarajan

[11] Patent Number: 4,623,703
[45] Date of Patent: Nov. 18, 1986

[54] SYNTHESIS OF CONDUCTING POLYMERS: POLYBUTADIENES FROM DISUBSTITUTED BUTYNES

[75] Inventor: Budalur S. Thyagarajan, San Antonio, Tex.

[73] Assignee: The University of Texas System, Austin, Tex.

[21] Appl. No.: 664,342

[22] Filed: Oct. 24, 1984

[51] Int. Cl.$^4$ .............................................. C08F 38/00
[52] U.S. Cl. .................................... 525/535; 528/376; 526/285
[58] Field of Search .................. 528/376; 526/285; 525/535

[56] References Cited

U.S. PATENT DOCUMENTS

| | | | |
|---|---|---|---|
| 2,351,108 | 6/1944 | Collins | 528/376 |
| 2,888,442 | 5/1959 | Uraneck et al. | 526/285 |
| 3,051,693 | 8/1962 | Leto | 526/285 |
| 3,717,618 | 2/1973 | Oswald | 526/285 |
| 3,751,511 | 8/1973 | Kay et al. | 260/680 |
| 3,755,489 | 8/1973 | Roberts et al. | 260/630 |
| 4,200,716 | 4/1980 | Pez | 526/170 |
| 4,228,060 | 10/1980 | Pez | 526/170 |
| 4,277,588 | 7/1981 | Naarmann et al. | 526/114 |
| 4,321,114 | 3/1982 | MacDiarmid et al. | 204/131 |

FOREIGN PATENT DOCUMENTS 1123724 8/1968 United Kingdom ................ 526/285

OTHER PUBLICATIONS

J. Chem. Soc., ©1971—Smith et al., pp. 1530–1535.
1982 American Chemical Society, Hiranuma et al., pp. 5083–5088.
J. Chem. Soc., ©1982, Bridges et al., pp. 665–666.
Tetrahedron Letters, vol. 23, No. 46, pp. 4763–4764, 1982, Jeganathan et al.
J. Org. Chem. 1984, 49, pp. 2954–2961, Bridges et al.
Chem. Abstracts: vol. 77, 1972, 6961a, vol. 70, 1971, 21197h, 5647g, vol. 58, 1970, 115012m, 60828y, vol. 96, 1982, 35775r.
Chem. Abstracts: vol. 94, 1981, 175630y, vol. 98, 1983, 54547a.
Polymer Communications, vol. 21, Jun., 1980, Edwards et al.
Chemistry of Organic Compounds by Noller, p. 240.
L. E. Callihan et al., "Synthesis of 1,2-Butadiene, Vapor Phase Isomerization of 2-Butyne Over Base–Modified Catalysts", 14 Ind. Eng. Chem., Prod. Res. Dev., 287–90 (1975).
G. R. Newkome et al, "Chemistry of Heterocyclic Compounds", 11 J. Heterocycl. Chem., 831–2 (1974).
J. W. Scheeren et al, "Synthesis of 1,1,4,4-Tetraalkoxy-1,3-Butadienes", 12 Tetrahedron Letters, No. 12, 1019–20 (1974).
K. Sato et al, "Isomerization of Butynes to 1,3-Butadiene Over Solid Base Catalysts", 11 Chem. Lett., 181–2 (1982).
K. Soga et al, "The Relationship of the Conductivity of Polyacetylene to the Average Length of Double-Bond Conjugation", J. Chem. Soc. Chem. Commun., 1495–6 (1983).
Y. Ikeda et al, "Synthesis of Poly(vinylene sulphied) and Its Electrical Properties," J. Chem. Soc. Chem. Commun., 1518–19 (1983).
M. R. Bryce et al, "Organic Metals", 309 Nature, 119–126 (May 1984).
S. Ramakanth et al, "An Unexpected Isomerisation of 1,4-Diaryloxy-2-Butynes to Z,Z-1,4-Diaryloxy-1,3-Butadienes–Potential Dienes for Diels–Alder Reaction", 25 Tetrahedron Letters 103–104 (1984).

Primary Examiner—Joseph L. Schofer
Assistant Examiner—N. Sarofim
Attorney, Agent, or Firm—Arnold, White & Durkee

[57] ABSTRACT

A two-step method is disclosed for chemically synthesizing substituted butadiene polymers from 1,4-disubstituted butynes. The first step in the synthesis of the butadiene polymer is the polymerization of 1,4-disubstituted butyne monomers. The substituted butyne polymer which results is then isomerized to the corresponding substituted butadiene polymer by subjecting the butyne to a weak organic base such as triethylamine. The isomerization reaction can be performed under very mild conditions and proceeds at ambient temperature.

1 Claim, No Drawings

SYNTHESIS OF CONDUCTING POLYMERS: POLYBUTADIENES FROM DISUBSTITUTED BUTYNES

BACKGROUND OF THE INVENTION

The present invention relates to the synthesis of butadienes and conjugated polyacetylenes from butyne-containing monomers. More particularly, the invention provides for the formation of both mono- and poly-1,4-diarylsulfonyl-1,3-butadienes from the corresponding mono- or poly-1,4-diarylsulfonyl-2-butynes under mild basic conditions in an organic solvent at ambient temperature.

Electroactive polymers have been the focus of a great deal of research in the last few years. Although organic solids have traditionally been thought of as electrical insulators, recent discoveries have demonstrated that a number of molecular crystals and organic polymers exhibit semiconductivity and even superconductivity. Due to their conductive properties, electroactive polymers have been referred to as "molecular metals". The unique properties exhibited by this new class of "molecular metals" offer great promise as conductors and semiconductors while carrying the potential benefits associated with polymers: they are inexpensive, strong, and easily processed into fibers, films, and coatings on an industrial scale. Numerous applications have been envisioned for electrically conducting organics ranging from lightweight batteries made from conducting polymer electrodes to less expensive electronic chips and semiconductors.

In general, the "molecular metals" fall into three classes. The first class consists of compounds containing metal chains. Materials in this group are characterized as either inorganic salts, such as the Krogmann salts, or metal ions, such as Pt or Ni, surrounded by organic ligands.

The second class of organic conductors, referred to as charge transfer complexes, are composed of organic crystals. Although organic crystals containing a single neutral species generally exhibit very low specific electrical conductivities, charge transfer crystals can exhibit high electrical conductivity. This group is characterized by mixed electron donor-acceptors such as tetrathiofulvalene-tetracyanoquinodimethane (TTF-TCNQ). The conductivities of these compounds generally increase upon cooling below 300° K. until approximately 60° K. when they undergo a Peierls transition and become semiconducting.

The third class of organic conductors, the conjugated polymers, are the subject of the present invention. Interest in this group began with the discovery that acetylene could be polymerized to a shiny black film, polyacetylene, which became highly conducting when "doped" by reaction with large amounts of strong oxidizing or reducing agents. The conductivity of the conjugated polymers is thought to be attributable to the ease of electron transport along the chain. Unfortunately, one of the principal problems presented by the conjugated polymers is that their chain rigidity and strong interchain forces tend to make them insoluble, infusible black powders.

One route which is being used to circumvent this problem is to prepare a flexible soluble precursor polymer which can be precast into films and converted into the corresponding polyacetylene. Researchers have attempted to utilize polyvinylchloride (PVC) in this manner due to the observation that upon heating, PVC releases HCl leaving a black polyacetylene-like material. Unfortunately, the resulting material is non-conductive. Presumably, the random loss of HCl pairs results in isolated Cl or H atoms which break up the conjugated sequences. Other investigators have dealt with this problem with some success by pairing up the leaving groups in the starting polymer, resulting in a more uniform polyacetylene structure. Yet, such structures often exhibit vastly different electrical properties relative to the polymer prepared by direct polymerization and they are quite difficult to chemically characterize.

Other approaches that have been investigated include modifying the polymer through copolymerization with agents such as polymethylacetylene in order to increase chain flexibility, but apparently this results in dramatic reductions in conductivity. In light of the above-mentioned problems in the development of electrical-conducting polymers, it is desirable that new methods be developed whereby polymers with increased solubility and a more uniform polymeric structure may be produced. Furthermore, it would be of additional benefit to develop methods whereby organic polymers exhibiting variations in their molecular geometry might be produced. It is possible that such geometrical variants of organic polymers might exhibit dissimilar variations in their resulting electrical properties.

In addition to the need for polymeric butadienes in the electroconductor field, butadiene-containing monomers have long been useful in the synthesis of synthetic rubber. For example, manufacture of synthetic rubber, latex paints, and nylon account for nearly all the butadiene consumed in the United States. Most of this butadiene is presently made by the expensive method involving dehydrogenation of normal butylenes and butanes or by steam cracking of naphthas. Accordingly, a less expensive and simpler method of producing monomeric butadienes is needed.

SUMMARY OF THE INVENTION

A method for chemically synthesizing a polybutadiene from a 1,4-disubstituted-2-butyne such as 1,4-diarylsulfonyl-2-butyne is provided. The method includes the steps of polymerizing the 1,4-disubstituted-2-butyne to the corresponding polybutyne followed by isomerization of the polybutyne to the corresponding polybutadiene. The isomerization step is accomplished by subjecting the polybutyne to a tertiary amine base such as triethylamine, diaminobocyclooctane, N-methyl piperidine, or n-methylmorpholine.

In addition, monomeric 1,4-disubstituted-2-butyne molecules, such as 1,4-diarylsulfonyl-2-butyne, may be isomerized to the corresponding 1,4-diarylsulfonyl-1,3-butadiene by subjecting the butyne-containing molecule to a tertiary amine base under conditions similar to those employed for isomerization of the polymer.

DETAILED DESCRIPTION OF THE PREFERRED EMBODIMENTS

The present invention offers the promise of circumventing many of the above-mentioned problems while creating vast potential in the area of soluble conducting polymers. The present invention accomplishes this by providing methods whereby substituted polybutynes may be converted to their corresponding polybutadienes. The preparation of substituted polyacetylenes, as embodied in the present invention, proceeds through two steps: polymerization of the butyne-containing monomers followed by base-catalyzed isomerization of the butyne moieties to butadienes. Moreover, the method of base-catalyzed isomerization of butyne structures to the corresponding butadienes is also applicable to non-polymerized butyne-containing monomers.

As used within the present application, the term butyne-containing molecule refers to an organic molecule, either monomeric or polymeric, which contains a 2-butyne moiety. Examples of butyne-containing molecules include 1,4-dichloro-2-butyne, 1,4-dibromo-2-butyne, 1,4-diarylsulfonyl-2-butyne, and polymers of 1,4-diarylsulfonyl-2-butyne or 1-S-aryl-(1',4')-dimercapto-2-butyne (i.e.—polyaryldimercaptobutyne). The term 1,4-disubstituted-2-butyne refers to monomeric butynes which are substituted at the 1 and 4 positions.

In the practice of one embodiment of the present invention, 1,4-dichloro-2-butyne (or 1,4-dibromo-2-butyne) is synthesized into the corresponding 1-S-aryl-(1',4')-dimercapto-2-butyne polymer. This is accomplished by reacting 1,4-benzenedithiol with either 1,4-dichloro-2-butyne or 1,4-dibromo-2-butyne in an organic solvent.

More specifically, a solution of KOH in methanol is first prepared using a stoichiometric ratio of one equivalent of KOH for each equivalent of thiophenol to be subsequently used. A solution of an appropriate thiophenol, such as 1,4-benzenedithiol, is added at room temperature in a dropwise fashion to a well-stirred solution of methanolic KOH. The addition should be made under a nitrogen blanket to prevent the oxidation of the thiophenol or its salt to the radical. After completing the addition of the thiophenol, the mixture is stirred at ambient temperature overnight. The potassium chloride formed in the reaction is filtered off, and the filtrate evaporated under a vacuum. The residual oil is extracted with chloroform and the chloroform extracts washed with 2.0M KOH solution and then with distilled water to remove all alkali. The chloroform solution is then dried over $Na_2SO_4$, and the solution evaporated under a vacuum. The remaining oil is distilled under a high vacuum to yield the butyne polymer. If the residue after removing the chloroform in the above reaction is a solid, it can be purified by recrystallization from a suitable solvent such as benzene/petroleum ether or chloroform/petroleum ether.

This reaction yields a polymer of 1-S-aryl-(1',4')-dimercapto-2-butyne, hereinafter referred to as polyaryldimercaptolbutyne, as shown below:

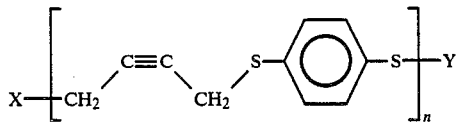

wherein on terminal monomeric units X and Y are hydrogen atoms.

The next step in the synthesis of the polyaryldisulfonyl butadiene is the sulfoxidation of the polyaryldimercaptobutyne produced by the preceding polymerization reaction. Oxidation is desirable in that it increases the acidity of the protons and thereby appears to enhance the ease of isomerization, while at the same time promoting the transfer of electrons in the resultant electroconductive polymer.

The polyaryldimercaptobutyne is dissolved in a mixture of equal amounts of glacial acetic acid and ether (50:50). An excess of 30% hydrogen peroxide is added to the mixture to assure complete oxidation of the sulfide to the sulfone. The mixture is then refluxed very gently until all the sulfide groups have reacted and no starting sulfide can be detected in the solution. The mixture is cooled to room temperature and poured with good stirring into ice cold $H_2O$. The sulfone precipitates as a colorless solid and is filtered over a Buchner funnel under water-vacuum. It is dried in a vacuum and is usually suitable for further reactions as is. If not, it can be purified by further crystallization from organic solvents such as tetrahydrofuran (THF), dimethylformamide (DMF), dimethylsulfoxide (DMSO), or sulfolane (thiophan sulfone).

The next step in the preparation of the butadiene polymer is the base-catalyzed isomerization of the polybutyne. The isomerization of the butyne appears to be facilitated by the presence of the alternating arylsulfonyl moieties. Thus, the reaction proceeds under mild basic conditions at ambient or only slightly elevated temperatures (50° C.). Moreover, the reaction proceeds well in most organic solvents including benzene, DMF, DMSO, THF, sulfolane, or N-methylformamide.

Other possible acidifying functions may be employed in promoting the isomerization reaction. For example, the presence of carbonyl, cyanidic or sulfidic moieties at the 1,4 position of the butyne appear to further facilitate the butyne isomerization to butadiene. In addition to the facilitation aspect, inclusion of a further substituent of the 1,4 position of the butyne gives further control over the molecular geometry of the resulting polybutadiene.

One embodiment for the isomerization of butynes to butadienes utilizes a 4:1 molar ratio of butyne moieties to the weak organic base. A tertiary amine base such as triethylamine works well, but other tertiary amine bases including diaminobicyclooctane, N-methylpiperidine, or N-methylmorpholine will also support the isomerization. The reaction is performed in an organic solvent. The preferred solvent is benzene but numerous other organic solvents may be utilized including those listed in the previous section.

The reactants are mixed in a reaction vessel and the reaction allowed to proceed at about 50° C. under a nitrogen blanket for about 2 to 3 hours. After the mixture is chilled, the polyaryldisulfonylbutadiene product can be collected by filtration. The structure of the polyaryldisulfonylbutadiene product that is obtained, poly-1-S-aryl-(1',4') disulfonyl-1,3-butadiene, is shown below:

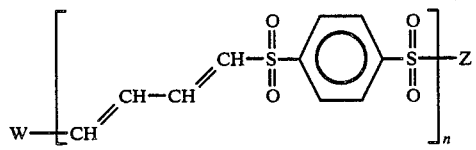

wherein on terminal monomeric units, W and Z are hydrogen atoms.

In addition to its applicability in the isomerization of butyne-containing polymers, base catalysis can also be utilized directly in the isomerization of butyne-containing monomers to the corresponding butadiene-containing molecules. For example, dibenzylsulfonylbutyne monomeric molecules, when subjected to a 0.25 molar ratio of a tertiary amine base, such as triethylamine, under a nitrogen blanket, will readily isomerize to the corresponding dibenzylsulfonylbutadiene.

The following examples are illustrative of the isomeric conversion of butyne-containing monomers.

EXAMPLE 1

1.8 grams (5 mmoles) of 1,4-di-p-tolylsulfonyl-2-butyne were dissolved in 100 ml. benzene and stirred with 0.13 grams triethylamine (1.25 mmoles) in 5 ml. benzene (1:0.25 molar equivalents of disulfone:triethylamine) at 50° C. under a nitrogen blanket for 3 hours. This mixture was then chilled in an ice bath yielding 0.76 grams of the butadiene as crop 1. The mother liquor was concentrated to approximately 20 ml. on a rotoevaporator and chilled in an ice bath, yielding 0.18 grams of the butadiene as crop 2. The melting point of crop 1 was 198°–200° C. and crop 2 was 196°–198° C. Combined crop 1 and crop 2 represented 51.7% of theoretical yield of 1,4-di-p-tolylsulfonyl-1,3-butadiene.

EXAMPLE 2

3.36 grams (10 mmoles) of 1,4-diphenylsulfonyl-2-butyne were dissolved in 175 ml. benzene and 0.25 grams of triethylamine were added (1:0.25 molar ratio). The mixture was stirred vigorously at 50° C. for 2.5 hours. The solution was allowed to cool to ambient temperature, then chilled in an ice bath and the resulting butadiene product collected by filtration. The actual yield of 1,4-diphenylsulfonyl-1,3-butadiene was 2.18 grams which exhibited a melting point of 177°–185° C. The actual yield was 65% of theoretical yield.

EXAMPLE 3

5.46 grams 1,4-diphenylsulfonyl-2-butyne (15 mmoles) were dissolved in 300 ml. benzene. 0.38 grams triethylamine (3.75 mmoles) were added and the mixture was stirred at 50° C. for 3 hours under an $N_2$ blanket. The solution was then chilled in an ice bath, petroleum ether added, and the flask scratched to afford a nucleation site for crystallization. 1.43 grams of the butadiene product were obtained as crop 1. The reaction was then continued by stirring the solution under nitrogen at 50° C. for 2 hours. The reaction vessel was chilled on ice and petroleum ether added to afford a second diene crop of 1.42 grams. The melting point of both crop 1 and crop 2 was 196°–199° C. The actual yield of 2.85 grams represented 52.4% of theoretical yield of 1,4-diphenylsulfonyl-1-3-butadiene.

EXAMPLE 4

5.0 grams of 1,4-di-p-tolylsulfonyl-2-butyne (13.7 mmoles) were refluxed in 100 ml. benzene under a nitrogen blanket. 0.35 grams of triethylamine (3.4 mmoles) were then added through the condensor. Progress of the reaction was monitored by thin-layer chromatography at 30 minutes. After 43 minutes, the reaction was stopped by dropping the heat and allowing the mixture to cool to ambient temperature. Once cooled, the mixture was diluted with 300 ml. benzene and washed with two 200 ml. aliquots of dilute HCl. The aqueous washes were then back extracted with three 100 ml aliquots of chloroform. The benzene and chloroform solutions were washed separately with three 200 ml. aliquots of $H_2O$ and dried over $Na_2SO_4$. The organic solutions were then combined and concentrated to approximately 100 ml. on the rotoevaporator. Chilling resulted in precipitation of the butadiene product which was collected in 5 crops. A total of 2.65 grams of the 1,4-di-p-tolylsulfonyl-1,3-butadiene were collected which represented 60% of the theoretical yield.

EXAMPLE 5

9.0 grams 1,4-di-p-tolylsulfonyl-2-butyne (24.7 mmoles) were refluxed for 30 minutes in 150 ml. benzene. 0.62 grams triethylamine (6.2 mmoles) were then added through the condensor and refluxing continued. Progress of the reaction was monitored every 5 minutes by thin-layer chromatography. After 40 min. the reaction was allowed to cool to ambient temperature and the resulting precipitate collected. The mixture was further chilled on ice to afford a second crop of the diene product. The reaction mixture was washed with two 200 ml. aliquots of dilute HCl solution followed by two 200 ml. $H_2O$ washes. After drying over $Na_2SO_4$, the reaction mixture was concentrated to approximately 40 ml. on the rotoevaporator, chilled on ice, and a final crop of butadiene product collected. The 5.13 grams of 1,4-di-p-tolylsulfonyl-1,3-butadiene represented 57% of theoretical yield.

EXAMPLE 6

5 grams of 1,4-di-p-tolylsulfonyl-2-butyne were dissolved in a solution containing 67 ml. freshly distilled benzene and 33 ml. of dimethylformamide. This solution was brought to a reflux following which a solution containing 20 ml. of $D_2O$ and 1.4 grams of triethylamine was poured into the reaction vessel. The reaction mixture was stirred vigorously at 50° C. to ensure complete mixing of aqueous and organic phases. After 40 minutes, the reaction mixture was allowed to cool to ambient temperatures and diluted with 400 ml. of benzene, washed with three 200 ml. aliquots of dilute HCl and four 300 ml. aliquots of $H_2O$. After drying over $Na_2SO_4$ and concentrating to 70 ml., a first crop of 2.32 grams of butadiene product was collected by filtration. The filtrate was further concentrated to approximately 25 ml. which, upon cooling, afforded a second crop of 0.53 grams of the butadiene product. The 2.85 grams of 1,4-di-p-tolylsulfonyl-1,3-butadiene represented 57% of the theoretical yield.

EXAMPLE 7

0.5 grams of 1,4-di-p-chlorophenylsulfonyl-2-butyne (1.25 mmoles) in 40 ml. benzene was combined with 0.6 ml. benzene:triethylamine (1:10 w/v) in a 100 ml. round-bottomed flask with a stir bar. $N_2$ was bubbled through the solution for 30 minutes. The mixture was then placed in a hot water bath for 3 minutes to increase the solubility of the bis-sulfone. The reaction was allowed to proceed for 70 minutes in a hot water bath and, after cooling, the butadiene product was collected by filtration. The reaction yielded 0.24 grams of 1,4-di-p-chlorophenylsulfonyl-1,3-butadiene representing 47% of theoretical yield.

EXAMPLE 8

2.01 grams of 1,4-di-p-chlorophenylsulfonyl-2-butyne were dissolved in a minimal amount of benzene (approx. 80 ml.) in a round-bottomed flask which was placed in a hot water bath (100° C.). 0.13 grams of triethylamine was added to the hot solution. The reaction mixture was stirred under $N_2$ while the temperature was allowed to equilabrate to room temperature. The mixture was then chilled, filtered, and washed with petroleum ether to remove the triethylamine. The butadiene product was recrystallized from chloroform/methanol yielding 1.25 grams which represented 62.5% of theoretical yield. The melting point of the 1,4-di-p-chlorophenylsulfonyl-1,3-butadiene was 230°–235° C.

EXAMPLE 9

5 grams of 1,4-di-p-tolylsulfonyl-2-butyne were dissolved in 96 ml. of benzene and 4 ml. of dimethylformamide in a 250 ml. round-bottomed flask and were refluxed. 0.35 grams of triethylamine was then pipetted in through the reflux condenser. The reaction temperature was allowed to equilibrate to room temperature.

The reaction mixture was diluted with 350 ml. of benzene and washed with two 250 ml. aliquots of dilute acid solution. An emulsion accrued at the interface which was removed with the acid layer which was then backextracted with chloroform. The chloroform layer was washed twice with 50 ml. of $H_2O$, dried over $Na_2SO_4$, filtered and rotoevaporated down to an oil which was washed with ether and yielded 0.1 grams of the butadiene product.

The original benzene layer was washed with four 150 ml. aliquots of $H_2O$, dried over $Na_2SO_4$, filtered, and rotoevaporated down to approximately 40 ml. This solution was chilled and filtered, yielding 2.43 grams of the butadiene product which exhibited a melting point of 200°–205°. The total yield of 2.53 grams of 1,4di-p-tolylsulfonyl-1,3-butadiene represented 51% of theoretical yield.

EXAMPLE 10

5.99 grams of 1,4di-phenylsulfonyl-2-butyne in 110 ml. of benzene were added to a 250 ml. round-bottomed flask. A reflux condenser was attached and the mixture was set to reflux. 6.46 ml. of a 0.1% triethylamine (w/v in benzene) solution was added through the condenser.

The reaction vessel was allowed to equilibrate to room temperature. The mixture was then chilled and filtered yielding 4.23 grams of the butadiene product.

The mother liquor was washed with two 150 ml. aliquots of dilute acid solution followed by two 150 ml. $H_2O$ washes, dried over $Na_2SO_4$, filtered, and rotoevaporated down to approximately 30 ml. Upon chilling, a second crop of 0.13 grams of the butadiene product were obtained. The total yield of 4.36 grams of 1,4-diphyenylsulfonyl-1,3-butadiene represented 73% of the theoretical yield.

The instant invention has been disclosed in connection with standard laboratory procedures used by the applicant. However, it will be apparent to those skilled in the art that variations for the illustrated procedures may be undertaken without departing from the spirit and scope of the invention. For example, a number of organic solvents will work equally well as the two organic solvents employed in above examples of butyne isomerization. Additionally, variations in the length of reaction time and reaction temperature have been demonstrated in the examples to have only a slight effect on the actual yield of butadiene product. These and other variations will be apparent to those skilled in the art and are within the spirit and scope of the invention.

What is claimed is:

1. A method for chemically synthesizing poly-1-S-aryl-(1′,4′)-disulfonyl-1,3-butadiene from 1,4-dichloro-2-butyne comprising the steps of:
    (a) reacting 1,4-dichloro-2-butyne with 1,4-benzenethiol to yield poly-1-S-aryl-(1′,4′)-dimercapto-2-butyne;
    (b) oxidizing sulfide groups in the 1-S-aryl-(1′,4′)-dimercapto-2-butyne polymer to corresponding sulfonyls to yield poly-1-S-aryl-(1′,4′)-disulfonyl-2-butyne; and
    (c) isomerizing the poly-1-S-aryl-(1′,4′)-disulfonyl-2-butyne to yield the poly-1-S-aryl-(1′,4′)-disulfonyl-1,3-butadiene.

* * * * *